United States Patent [19]

Kubo et al.

[11] 3,984,477

[45] Oct. 5, 1976

[54] CATALYST FOR PRODUCTION OF $\alpha,\beta$-UNSATURATED ALDEHYDES

[75] Inventors: Masayochi Kubo; Kazuyuki Matsuoka; Takushi Yokoyama, all of Ohimachi, Japan

[73] Assignee: Daicel, Ltd., Osaka, Japan

[22] Filed: Dec. 10, 1974

[21] Appl. No.: 531,317

[30] Foreign Application Priority Data

Dec. 11, 1973 Japan.............................. 48-139334
Oct. 3, 1974 Japan.............................. 49-114126
Oct. 3, 1974 Japan.............................. 49-114127

[52] U.S. Cl............................. 260/604 R; 252/432; 252/437; 252/470
[51] Int. Cl.².................. C07C 45/04; B01J 21/02; B01J 23/84; B01J 27/18
[58] Field of Search .......... 252/464, 470, 432, 437; 260/604 R

[56] References Cited
UNITED STATES PATENTS

| | | | |
|---|---|---|---|
| 3,171,859 | 3/1965 | Sennewald et al.............. | 252/470 X |
| 3,642,930 | 2/1972 | Grasselli et al. .................... | 252/464 |
| 3,778,386 | 12/1973 | Takenaka et al. .................. | 252/470 |
| 3,786,000 | 1/1974 | Ono et al........................ | 252/470 X |
| 3,804,903 | 4/1974 | Hagiwara ........................ | 260/604 R |

*Primary Examiner*—W. J. Shine
*Attorney, Agent, or Firm*—Woodhams, Blanchard and Flynn

[57] ABSTRACT

A catalyst for preparing $\alpha,\beta$-unsaturated aldehydes by the gas phase catalytic oxidation of $\alpha,\beta$-unsaturated hydrocarbons, which catalyst contains as indispensable metal components molybdenum, bismuth and at least one transition metal selected from iron, nickel and cobalt. A chelating agent, or a chelate compound of any of the metals comprising the catalyst, is added to all or some of the starting liquid mixtures during the catalyst preparation stage, whereby to increase the catalytic activity of the catalyst so that the desired $\alpha,\beta$-unsaturated aldehyde products such as acrolein and methacrolein can be obtained in high yields. In catalysts of this type, the catalytic activity can be maintained at a high level even if the catalyst does not contain an arsenic component.

6 Claims, No Drawings

CATALYST FOR PRODUCTION OF α,β-UNSATURATED ALDEHYDES

BACKGROUND OF THE INVENTION

1. Field of the Invention

This invention relates to a catalyst for use in preparing α,β-unsaturated aldehydes. More particularly, the invention relates to the preparation of a catalyst characterized in that a chelating agent or a macromolecular chelating agent, or a reaction product of a chelating agent and any of the catalyst metals having the form of a chelate compound or macromolecular chelate compound, is added during the catalyst preparation stage. Especially, this invention provides a catalyst having a highly enhanced activity for producing α,β-unsaturated aldehydes by gas phase catalytic oxidation of α,β-unsaturated hydrocarbons.

2. Description of the Prior Art

It is well known in the art that metal oxide catalysts comprising as main metal components molybdenum, bismuth and a transition metal, especially iron, cobalt or nickel, and optionally containing other elements incorporated according to need, can be used for the gas phase catalytic oxidation of α,β-unsaturated hydrocarbons to produce α,β-unsaturated aldehydes. Conventional catalysts of this type, however, have various defects.

These known catalysts include at least 5 metals as constitutuent metals and they can contain more than 10 metals in some cases. Accordingly, the catalyst system is very complicated and the preparation of such catalysts involves various problems and difficulties. There is a risk that reproducible catalytic activity cannot be obtained. Moreover, in many cases, expensive metals or toxic substances are used in the catalyst.

For example, an oxide catalyst of the Mo-Fe-Bi-As system disclosed in Japanese Patent Publication No 4771/69 and an oxide catalyst of the Mo-Bi-Co-Ni-Fe-As system disclosed in Japanese Patent Publication No. 6246/69 contain a poisonous substance, such as arsenic oxide, as a component for improving the yield of the α,β-unsaturated aldehyde product. Therefore, these catalysts involve a risk that a poisonous substance, such as arsenic, can be discharged outside the reaction system, under some reaction conditions or depending on the working process. What is more important is that since arsenic compounds are very toxic and harmful, there is a danger that workers will suffer serious injury during preparation of arsenic-containing catalysts or during handling of such catalysts, for example, when withdrawing them from the reaction vessel. Accordingly, a process for preparing α,β-unsaturated aldehydes that uses a catalyst containing an arsenic compound cannot be regarded as an industrially optimum process.

Catalysts comprising as main components, for example, oxides of Mo, Bi and Fe, are generally prepared by a method comprising dissolving ammonium molybdate in water, separately forming an aqueous solution of ferric nitrate and bismuth nitrate acidified with nitric acid, mixing this acidified aqueous solution with the above solution of ammonium molybdate, adding a suitable carrier and other salts to the liquid mixture according to need, and then conducting the conventional concentration, drying, molding and calcination steps to prepare the final catalyst composition.

The thus-prepared oxide catalysts of the Mo-Bi-Fe system have a lower catalytic activity than the oxide catalysts of the Mo-Bi-Fe-As system disclosed in Japanese Patent Publication No. 4771/69. It is difficult to produce α,β-unsaturated aldehydes on an industrial and economically advantageous scale using such oxide catalysts of the Mo-Bi-Fe system. Further, in preparing such catalysts, molybdenum reacts with iron to form a gel-like precipitate, thereby degrading the dispersed state of the metals and resulting in a difficulty of obtaining reproducible results in the preparation of the catalysts. Moreover, the formation of the gel-like precipitate during the catalyst preparation stage causes a reduction of the catalytic activity of the resulting catalysts.

SUMMARY OF THE INVENTION

We have discovered that unique catalysts of the molybdenum-bismuth-transition metal type, useful for the production of α,β-unsaturated aldehydes and possessing important advantages, are obtained by adding a chelating agent, or by employing any of the constituent metals of the catalyst in the form of a chelate compound, during the catalyst preparation stage. The resulting catalyst has a highly enhanced catalytic activity.

The role of the arsenic component in an oxide catalyst of the As-Mo-Bi-Fe system has been investigated with a view to overcoming the above-mentioned disadvantages of the arsenic component. It was found that when a chelating agent is added, instead of arsenic, during the catalyst preparation stage, or when any of the catalyst metals is added in the form of a metal chelate compound, instead of using an arsenic compound, the resulting catalyst possesses a high activity for the gas phase catalytic oxidation of olefins.

According to the invention, a highly active catalyst is prepared in the following manner. Ammonium molybdate is dissolved in water, and a chelating agent is added thereto and is completely dissolved in the solution. Separately, iron nitrate and bismuth nitate are dissolved in an aqueous solution acidified with nitric acid to a pH in the range of below 6. Then, the above aqueous solution of ammonium molybdate is added to the thus-formed acidified aqueous solution, and, optionally, a carrier is added thereto, according to need. The liquid mixture is concentrated and dried by heating in air at a temperature below about 200° C. The resulting dried product is treated in an air current, at a temperature in the range of 200° to 400° C., to decompose the nitrates, and is molded and calcined, at a temperature in the range of 400° to 700° C., to obtain a catalyst.

The chelating agent can be added to either the aqueous solution of ammonium molybdate, or to the nitric acid-acidifed aqueous solution of iron nitrate and bismuth nitrate, or to both solutions. Also, the same unexpectedly improved effect can be obtained when there is employed a chelate compound previously formed by reaction between the chelating agent and any of the metal components of the catalyst. Further, the same effects can be similarly attained by addition of the chelating agent or the chelate compound during the preparation of catalysts that contain, in addition to the above-mentioned Mo, Bi and Fe, additional elements of Groups, I, III, V and VI of the Periodic Table such as an alkali metal selected from the group consisting of K, Rb and Cs, W, P, B, and the like. Thus, the improved effects attained by addition of the chelating agent or chelate compound are not limited to oxide catalysts of the Mo-Bi-Fe system. Similar results can be obtained when Ni or Co is used as the transition metal, instead of Fe. Another interesting discovery is that in the case of catalysts of the Mo-Bi-Fe (or Ni or Co)-As system, if a chelating agent or metal chelate compound is added during the catalyst preparation stage the catalytic activity of such arsenic-containing catalyst also significantly increases. In view of these facts, it is concluded that the chelating agent contributes greatly to improvement of the catalytic activity.

The chelating agent is volatized during the subsequent steps of the process and it disappears completely by the end of the calcination step. Thus, the improved catalytic properties of the catalyst according to the invention are not caused by the presence of chelating agent therein, but rather are believed to be due to some unique interaction or combination of metals caused by the presence of the chelating agent during mixing of the aqueous solutions. This phenomenon has not been explained to date.

As is apparent from the foregoing, the initial discovery resided in the substitution of a chelating agent for arsenic compounds. But as a result of further study, it was found that the catalytic activity of arsenic-containing catalysts can also be greatly increased by addition of a chelating agent. Accordingly, this invention is of broad applicability to catalysts containing molybdenum, bismuth and a transition metal, as essential metal components, and optionally containing various other metals, and used for the production of $\alpha,\beta$-unsaturated aldehydes. According to this invention, a catalysts having a valuable high activity can be obtained even if no arsenic component is present.

More specifically, in accordance with this invention, there is provided a catalyst for preparing $\alpha,\beta$-unsaturated aldehydes by the gas phase catalytic oxidation of $\alpha,\beta$-unsaturated hydrocarbons, which catalyst comprises as critical metal components (a) molybdenum, (b) bismuth and (c) at least one transition metal selected from the group consisting of iron, nickel and cobalt. The catalyst is prepared by adding during the catalyst preparation stage at least one catalyst-improving member selected from the group consisting of (a) chelating agents and (b) metal chelate compounds obtained by reaction in advance of the catalyst preparation stage between the chelating agent and at least one of the component metals to be incorporated in the catalyst. The catalyst-improving member is added to all or some of the starting liquid mixtures during the catalyst preparation stage.

According to this invention, a chelating agent (a) or metal chelate compound (b) is added to an otherwise known catalyst system to improve the catalytic activity of the catalyst system, whereby the yields of the desired $\alpha,\beta$-unsaturated aldehyde products such as acrolein are highly improved. Further, according to this invention, a high catalytic activity can be obtained using catalyst systems free of poisonous components such as arsenic compounds.

DETAILED DESCRIPTION OF THE PREFERRED EMBODIMENTS

Various chelating agents can be used for preparing the catalyst of this invention. The chelating agents to be employed in this invention are organic compounds which are substantially completely subject to volatilization or combustion or oxidation to hydrogen oxide, carbon oxide and nitrogen oxide from the catalyst at the calcination temperature range, or lower temperatures.

They are furthermore defined as organic compounds able to be subjected to the interaction with metals or polydentate. That is, they have in their molecules two or more atoms or atomic groups able to coordinate metals.

In case that the chelating agents are macromolecular, the molecular weight thereof is not necessary to be defined.

They are defined as water-soluble macro molecular chelating agents having two or more functional groups able to bond to metals, such as -OH, -COOH, >C=O, —O-, -N=O, -NO$_2$, -SO$_3$H-, -NH$_2$, >NH, ≡N, -CONH$_2$, -N=N-, =N-OH, =C=NR,

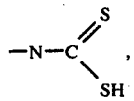

-SCN, -SH, >C=S,

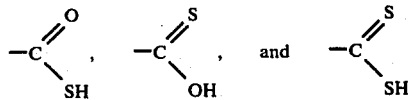

As the chelating agent that can be used in this invention, for example, dicarboxylic acids such as, malonic acid, oxalic acid, phthalic acid, succinic acid, maleic acid, citraconic acid and itaconic acid, aliphatic amines such as ethylenediamine, N,N'-dimethylethylenediamine, diethylenetramine, $\beta,\beta,'\beta''$-triaminotriethylamine, diethyltriamine, propylenediamine and 1,2,3-triaminopropanes; aromatic amines such as 2,2'-dipyridyl, phenanthroline and derivatives thereof; natural amino acids and peptides such as alanine, $\beta$-alanine, glycylalanine, asparagine, asparagic acid, glycine, glycidylglycine, glutamic acid, histidine, leucine, methionine, phenylalanine, proline, tryptophane, cerin, tyrosine and valine; synthetic amino acids such as $\beta$-alanine-N,N'-diacetic acid, aminobarbituric acid-N,N'-diacetic acid, 3-aminobenzoic acid-N,N-diacetic acid, 2-phosphonoethylimino-N,N-diacetic acid, aminomethylphosphonic acid-N,N-diacetic acid, iminodiacetic acid, nitrilotriacetic acid, ethylenediamine-tetraacetic acid and N-benzylethylenediamine-triacetic acid; hydroxy acids such as citric acid, gluconic acid, glyceric acid, glucolic acid, $\beta$-hydroxybutyric acid and tartaric acid; $\beta$-diketones such as acetylacetone, benzylacetone and benzylmethanefuroylacetone; and aminobenzenethiol, aminophenol and ethyl acetoacetate.

Macromolecular chelating agents can also be used for preparing the catalyst of this invention. As the macromolecular chelating agent, here can be mentioned, for example, polycarboxylic acids such as polymers of acrylic acid, or maleic anhydride, copolymers of acrylic acid and methacrylic acid, acrylic acid copolymers, allyl alcohol copolymrs, polycarboxylic acids prepared by the Cannizzaro reaction of a polymer of acrolein, polyacrylamides and the like.

The amount of chelating agent, whether added as such during the catalyst preparation stage or reacted in advance with at least one of the component metals of the catalyst, is in the range of from 0.1 to 60 percent by weight, preferably 0.5 to 50 percent by weight, more preferably 0.8 to 30 percent by weight based on the metal content of the final catalyst composition.

Any inert carriers or supports for catalysts customarily used in this field, such as silica, silica-alumina, diatomaceous earth and pumice can be used in the catalyst composition of this invention.

The amounts of the metals in the final catalyst composition are not particularly critical in this invention and there can be used the known metal oxide catalyst compositions useful for the catalytic gas phase oxidation of α,β-olefinically unsaturated hydrocarbons to form α, β-olefinically unsaturated aldehydes. For examples, there can be used a metal oxide catalyst, the metal content of which is expressed by the following empirical formula $$(Mo)_a(Bi)_b(J)_c(L)_d(O)_e$$

wherein J is Fe, Co, Ni or mixtures thereof, L is one or more metals selected from the metals of Groups I, III, V and VI of the Periodic Table, and "a", "b", "c", "d" and "e" represent the number of atoms of Mo, Bi, J and L, and O, respectively, "a" being 12, "b" being 0.5 to 6, "c" being 3 to 30, "d" being 0 to 10 and "e" being the number of oxygen atoms sufficient to satisfy the tomic valences of Mo, Bi, J and L. Such catalysts are known in the art.

When the catatlysts of this invention are used for preparing α,β-unsaturated hydrocarbons with molecular oxygen, especially for converting propylene and isobutylene into corresponding unsaturated aldehyde compounds such as acrolein and methacrolein, the excellent effects mentioned above are attained and the intended products such as acrolein and methacrolein can be obtained in high yields. As is well known, this reaction is carried out in the gas phase, using a molecular oxygen-containing gas as oxidizing agent, at a temperature of 250° to 400°C. Further details of this process are disclosed in U.S. Serial No. 376 317, filed July 5, 1973, now U.S. Pat. 3,894,091.

The invention will now be described in more detail by reference to the following illustrative Examples.

EXAMPLE 1

18.68 g of ammonium molybdate [(NH$_4$)$_6$Mo$_7$O$_{24}$·4H$_2$O] and 2.58 g of ethylenediamine-tetraacetic acid [CH$_2$N(CH$_2$COOH)$_2$]$_2$ were dissolved under heating in 200 ml of water. Separately, 26.72 g of ferric nitrate [Fe(NO$_3$)$_3$·9H$_2$O], 8.56 g of bismuth nitrate [Bi(NO$_3$)$_3$·5H$_2$O] and 0.35 g of potassium nitrate (KNO$_3$) were dissolved under heating in 23 ml of a nitric acid-acidified aqueous solution and this solution was mixed with the above solution of ammonium molybdate. Then, 50 g of silica gel having a particle size of 150 mesh (Japanese Industrial Standard) or smaller was added to the mixture, and the mixture was heated and concentrated to form a slurry. The catalyst slurry was dried at 120°C. in air and then heated at 350°C. to decompose the nitrates. Then, the thus-treated catalytic composition was molded into cylindrical pellets having a diameter of 5 mm and a length of 3 mm and calcined at 560°C. in an air current. In the resulting metal oxide catalyst, the atomic ratio of the constituent metals was expressed as Mo$_{12}$Fe$_{7.5}$Bi$_2$K$_{0.4}$. The ethylenediamine-tetraacetic acid added during the catalyst preparation stage disappeared completely during the calcination step. A stainles steel U-shaped reaction tube having an inner diameter of 27 mm was charged with 60 ml of the thus-obtained catalyst and immersed in an molten salt bath consisting of 3 percent NaNO$_3$, 50 percent KNO$_3$ and 47 percent NaNO$_2$ by weight. A gaseous mixture containing 6 mole percent of propylene and 42.8 mole percent of air, with the balance being steam, was passed through the packed reaction vessel at a reaction temperature of 340°C. so that the contact time was 2.4 seconds. The following results were obtained:

Conversion of propylene: 94.1 mole %
Yield of acrolein: 74.7 mole %
Selectivity to acrolein: 79.4 mole %

Comparative Example 1

18.68 g of ammonium molybdate was dissolved under heating in 200 m of water. Separately, 26.72 g of ferric nitrate, 8.56 g of bismuth nitrate and 0.35 g of potassium nitrate were dissolved under heating in 23 ml of a nitric acid-acidified aqueous solution, and the resulting solution was mixed with the above solution of ammonium molybdate. In the same manner as in Example 1, the catalytic composition was molded into cylindrical pellets having a diameter of 5 mm and a length of 3 mm and calcined to obtain a catalyst.

The atomic ratio of the constituent metals in the thus-obtained metal oxide catalyst was expressed as Mo$_{12}$Fe$_{7.5}$Bi$_2$K$_{0.4}$. Under the same reaction conditions as in Example 1, gas phase catalytic oxidation of propylene was conducted by using a gaseous mixture having the same composition as in Example 1 and 60 ml of the thus-obtained catalyst. The following results were obtained:

Conversion of propylene: 86.6 mole %
Yield of acrolein: 66.5 mole %
Selectivity to acrolein: 76.8 mole %

By-products such as carbon dioxide gas, carbon monoxide and organic acids were formed in addition to acrolein.

When the results of Example 1 are compared with those of Comparative Example 1, it will readily be understood that the catalyst of the Mo-Fe-Bi-K system can be highly activated by employing ethylenediamine-tetraacetic acid during the catalyst preparation stage and that the activity for forming acrolein is highly enhanced over the comparative catalyst prepared without using ethylenediamine-tetraacetic acid.

EXAMPLE 2

A catalyst was prepared in the same manner as described in Example 1 except that the ethylenediamine-tetraacetic acid was not added to the aqueous solution of ammonium molybdate but rather was added to the nitric acid-acidified aqueous solution containing ferric nitrate, bismuth nitrate and potassium nitrate. In the same manner as in Example 1, gas phase catalytic oxidation of propylene was conducted by using the thus-obtained catalyst. The following results were obtained:

Conversion of propylene: 90.7 mole %
Yield of acrolein: 73.1 mole %
Selectivity to acrolein: 80.8 mole %

EXAMPLE 3 to 6

In the same manner as described in Example 2, catalysts were prepared by using various aminopolycarboxylic acids as listed in Table 1 below as the chelating agent instead of ethylenediamine-tetraacetic acid, and gas phase catalytic oxidation of propylene was carried out in the same manner as in Example 1 by using the thus-obtained catalysts. The results are shown in Table 1.

Table 1

| Example No. | Chelating Agent | Conversion (mole %) of propylene | Yield (mole %) of acrolein | Selectivity (mole %) to acrolein |
|---|---|---|---|---|
| 3 | glycoletherdiamine-tetraacetic acid | 91.8 | 74.8 | 81.4 |
| 4 | nitrilotriacetic acid | 93.7 | 74.4 | 79.4 |
| 5 | 1,2-diaminocyclohexane-tetraacetic acid | 89.4 | 69.1 | 77.3 |
| 6 | iminodiacetic acid | 83.1 | 70.5 | 84.6 |

EXAMPLES 7 to 9

Catalysts were prepared in the same manner as in Example 2 by using the carboxylic acids indicated in Table 2 as the chelating agent, and catalytic oxidation of propylene was conducted in the same manner as in Example 1 by using the thus-prepared catalyst. The results shown in Table 2 were obtained.

Table 2

| Example No. | Chelating Agent | Conversion (mole %) of propylene | Yield (mole %) of acrolein | Selectivity (mole %) to acrolein |
|---|---|---|---|---|
| 7 | malonic acid | 84.1 | 70.0 | 83.3 |
| 8 | oxalic acid | 89.2 | 70.4 | 78.9 |
| 9 | thiodipropionic acid | 89.5 | 71.0 | 79.3 |

EXAMPLES 10 and 11

Catalysts were prepared in the same manner as in Example 2 by using the amines listed in Table 3 as the chelating agent, and catalytic oxidation of propylene was conducted in the same manner as in Example 1 by using these catalysts. The results shown in Table 3 were obtained.

Table 3

| Example No. | Chelating Agent | Conversion (mole %) of propylene | Yield (mole %) of acrolein | Selectivity (mole %) to acrolein |
|---|---|---|---|---|
| 10 | diethylenetriamine | 88.3 | 70.7 | 80.0 |
| 11 | N,N'-di-n-butylthiourea | 91.7 | 73.1 | 79.7 |

EXAMPLES 12 to 15

Catalysts were prepared in the same manner as in Example 2 by using the amino acids listed in Table 4 as the chelating agent, and catalytic oxidation of propylene was carried out in the same manner as in Example 1 by using these catalysts. The results shown in Table 4 were obtained.

Table 4

| Example No. | Chelating Agent | Conversion (mole %) of propylene | Yield (mole %) of acrolein | Selectivity (mole %) to acrolein |
|---|---|---|---|---|
| 12 | β-alanine | 85.6 | 71.8 | 83.9 |
| 13 | asparagic acid | 86.1 | 70.4 | 81.8 |
| 14 | tyrosine | 83.2 | 71.7 | 86.3 |
| 15 | proline | 84.6 | 70.5 | 83.3 |

EXAMPLES 16 to 18

Catalysts were prepared in the same manner as in Example 2 by using the hydroxy acids indicated in Table 5 as the chelating agent, and catalytic oxidation of propylene was carried out in the same manner as in Example 1 by using these catalysts. The results shown in Table 5 were obtained.

Table 5

| Example No. | Chelating Agent | Conversion (mole %) of propylene | Yield (mole %) of acrolein | Selectivity (mole %) to acrolein |
|---|---|---|---|---|
| 16 | tartaric acid | 91.7 | 70.8 | 77.2 |
| 17 | citric acid | 88.1 | 72.1 | 81.8 |
| 18 | diglycolic acid | 88.8 | 73.0 | 82.3 |

EXAMPLE 19

18.68 g of ammonium molybdate was dissolved under heating in 200 ml of water. Separately, 21.38 g of ferric nitrate, 2.24 g of acetylacetone-iron, 8.56 g of bismuth nitrate and 0.35 g of potassium nitrate were dissolved under heating into 23 ml of a nitric acid-acidified aqueous solution. Subsequent treatments were conducted in the same manner as in Example 1 to obtain a catalyst. Catalytic oxidation of propylene was carried out in the same manner as in Example 1 by using the thus-prepared catalyst. The following results were obtained.

Conversion of propylene: 90.8 mole %
Yield of acrolein: 70.9 mole %
Selectivity to acrolein: 78.1 mole %

EXAMPLES 20 and 21

Catalysts were prepared in the same manner as in Example 2 by using the β-diketones indicated in Table 6 as the chelating agent, and catalytic oxidation of propylene was conducted in the same manner as in Example 2 by using these catalysts. The results shown in Table 6 were obtained.

Table 6

| Example No. | Chelating Agent | Conversion (mole %) of propylene | Yield (mole %) of acrolein | Selectivity (mole %) to acrolein |
|---|---|---|---|---|
| 20 | acetylacetone | 91.3 | 73.1 | 80.1 |
| 21 | benzoylacetone | 87.2 | 73.6 | 84.4 |

EXAMPLE 22

A catalyst was prepared in the same manner as in Example 1 except that o-aminophenol was used as the chelating agent. Catalytic oxidation of propylene was conducted in the same manner as in Example 1 by using the thus-prepared catalyst. The following results were obtained:
Conversion of propylene: 86.0 mole %
Yield of acrolein: 70.2 mole %
Selectivity to acrolein: 81.6 mole %

EXAMPLE 23

A catalyst was prepared in the same manner as in Example 1 except that 2-aminothiazole was used as the chelating agent, and catalytic oxidation of propylene was carried out in the same manner as in Example 1 by using the thus-prepared catalyst. The following results were obtained:
Conversion of propylene: 91.1 mole %
Yield of acrolein: 70.8 mole %
Selectivity to acrolein: 77.7 mole %

EXAMPLES 24 TO 33 AND COMPARATIVE EXAMPLES 2 TO 11

Catalysts were prepared by using ethylenediaminetetraacetate, or without using this chelating agent, in the same manner as decribed in Example 1 and Comparative Example 1. The catalyst composition was changed so that metal contents of the catalysts were as indicated in Table 7. Catalytic oxidation of propylene was carried out under the same conditions as in Example 1 by using the thus-prepared catalysts.

The resuls shown in Table 7 were obtained. From these results, it will readily be understood that the yield of acrolein is highly improved by addition of the chelating agent in each catalyst composition.

TABLE VII

| | Catalyst Composition | Chelating Agent used | Conversion (mole %) of propylene | Yield (mole %) of acrolein | Selectivity (mole %) to acrolein |
|---|---|---|---|---|---|
| Example 24 | $Mo_{12}Fe_{7.5}Bi_2Rb_{0.4}$ | ethylenediaminetetraacetate | 91.0 | 71.2 | 78.2 |
| Comparative Example 2 | '' | none | 82.4 | 63.6 | 77.2 |
| Example 25 | $Mo_{12}Fe_{7.5}Bi_2Cs_{0.4}$ | ethylenediaminetetraacetate | 92.6 | 74.8 | 80.8 |
| Comparative Example 3 | '' | none | 77.6 | 60.4 | 77.9 |
| Example 26 | $Mo_{12}Fe_{7.5}Bi_1K_{0.4}$ | ethylenediaminetetraacetate | 93.1 | 72.6 | 78.0 |
| Comparative Example 4 | '' | none | 80.6 | 59.8 | 74.2 |
| Example 27 | $Mo_{12}Fe_{7.5}Bi_4K_{0.4}$ | ethylenediaminetetraacetate | 87.0 | 70.9 | 81.5 |
| Comparative Example 5 | '' | none | 83.5 | 64.5 | 77.2 |
| Example 28 | $Mo_{12}Co_3Ni_1Fe_2Bi_1K_{0.3}$ | ethylenediaminetetraacetate | 79.2 | 62.0 | 78.3 |
| Comparative Example 6 | '' | none | 69.3 | 55.0 | 79.3 |
| Example 29 | $Mo_{12}W_2Co_4Fe_1Bi_1K_{0.3}$ | ethylenediaminetetraacetate | 47.3 | 30.2 | 63.9 |
| Comparative Example 7 | '' | none | 29.3 | 24.5 | 83.9 |
| Example 30 | $Mo_{12}41\ 75Bi_2As_{0.2}K_{0.3}$ | ethylenediaminetetraacetate | 92.8 | 74.2 | 79.9 |
| Comparative Example 8 | '' | none | 88.8 | 71.3 | 80.6 |
| Example 31 | $Mo_{12}Fe_{7.5}Bi_2As_{0.1}K_{0.3}$ | ethylenediaminetetraacetate | 92.4 | 73.1 | 79.1 |
| Comparative Example 9 | '' | none | 89.0 | 68.3 | 76.7 |
| Example 32 | $Mo_{12}Fe_{7.5}Bi_2P_{0.4}K_{0.3}$ | ethylenediaminetetraacetate | 93.9 | 75.2 | 80.1 |
| Comparative Example 10 | '' | none | 77.0 | 64.2 | 83.3 |
| Example 33 | $Mo_{12}Fe_{7.5}Bi_2B_{1.0}K_{0.4}$ | ethylenediaminetetraacetate | 91.4 | 73.9 | 80.8 |
| Comparative Example 11 | '' | none | 85.7 | 67.2 | 78.4 |

EXAMPLE 34

18.68 g of ammonium molybdate and 1 g of polyacrylic acid (product sold under tradename of "Julymer AC 10L" by Nippon Junyaku) were dissolved under heating in 200 ml of water. Separately, 26.72 g of ferric nitrate, 8.56 g of bismuth nitrate and 0.35 g of potassium nitrate were dissolved under heating in 25 ml of a nitric acid-acidified aqueous solution. The thus-formed aqueous solution was mixed with the above aqueous solution of ammonium molybdate. Subsequent treatments were conducted in the same manner as described in Example 1 to obtain a metal oxide catalyst in which the atomic ratio of the constituent metal elements is expressed as $Mo_{12}Fe_{7.5}Bi_2K_{0.4}$. The polyacrylic acid disappeared during the calcination step. Catalytic oxidation of propylene was conducted in the same manner as in Example 1 by using the thus-prepared catalyst. The following results were obtained:
Conversion of propylene: 86.9 mole %
Yield of acrolein: 73.7 mole %
Selectivity of acrolein: 84.5 mole %

When the above results are compared with the results obtained in Comparative Example 1 wherein no chelating agent was used, it will readily be understood that the catalyst is activated by the polyacrylic acid and the activity for producing acrolein is highly enhanced by the use of the macromolecular chelating agent over the comparative catalyst prepared without using the macromolecular chelating agent.

COMPARATIVE EXAMPLE 12

18.68 g of ammonium molybdate was dissolved under heating in 200 ml of water. Separately, 26.72 g of ferric nitrate, 8.56 g of bismuth nitrate, 0.35 g of potassium nitrate and 0.26 g of 85 percent phosphoric acid were dissolved under heating in 23 ml of a nitric acid-acidified aqueous solution, and the thus-formed aqueous solution was mixed with the above aqueous solution of ammonium molybdate. Subsequent treatments were conducted in the same manner as in Example 1 to obtain a metal oxide catalyst in which the atomic ratio of the constituent metal elements is expressed as $Mo_{12}Fe_{7.5}Bi_2K_{0.4}P_{0.3}$. Catalytic oxidation of propylene was conducted in the same manner as in Example 1 by using 60 ml of the thus-prepared catalyst. The following results were obtained:
Conversion of propylene: 77.0 mole %
Yield of acrolein: 64.2 mole %
Selectivity to acrolein: 83.3 mole %

EXAMPLE 35

A catalyst was prepared in the same manner as in Comparative Example 12 except that 1 g of polyacrylic acid was used as the macromolecular chelating agent, and catalytic oxidation of propylene was carried out in the same manner as in Example 1 by using the thus-obtained catalyst. The following results were obtained:
Conversion of propylene: 89.7 mole %
Yield of acrolein: 77.6 mole %
Selectivity to acrolein: 86.5 mole %

EXAMPLE 36

A catalyst was prepared in the same manner as in Comparative Example 12 except that 1 g of an acrylic acid-methacrylic acid copolymer (sold under tradename of "Julymer AC 20H") was used as the macromolecular chelating agent, and catalytic oxidation of propylene was carried out in the same manner as in Example 1 by using the thus-prepared catalyst. The following results were obtained:
Conversion of propylene: 88.0 mole %
Yield of acrolein: 75.6 mole %
Selectivity to acrolein: 85.9 mole %

EXAMPLE 37

A catalyst was prepared in the same manner as in Comparative Example 12 except that 2 g of polyhydroxycarboxylic acid was used as the macromolecular chelating agent, and catalytic oxidation of propylene was carried out in the same manner as in Example 1 by using the thus-prepared catalyst. The following results were obtained:
Conversion of propylene: 87.8 mole %
Yield of acrolein: 76.7 mole %
Selectivity to acrolein: 87.3 mole %

EXAMPLES 38 to 42 AND COMPARATIVE EXAMPLES 13 to 16

Catalysts were prepared by adding polyacrylic acid, or without adding polyacrylic acid, in the same manner as in Example 34 and Comparative Example 1, except that the catalyst composition was changed as indicated in Table 8. Catalytic oxidation of propylene was carried out in the same manner as in Example 1 by using the thus-prepared catalysts to obtain results shown in Table 8. From these results, it will readily be understood that the yield of acrolein is highly improved by addition of the chelating agent in each composition.

Table 8

| | Catalyst Composition | Macromolecular Chelating Agent | Conversion (mole %) of propylene | Yield mole %) of acrolein | Selectivity (mole %) to acrolein |
|---|---|---|---|---|---|
| Example 38 | $Mo_{12}Fe_{7.5}Bi_2Rb_{0.4}P_{0.3}$ | polyacrylic acid | 92.7 | 79.0 | 85.2 |
| Comparative Example 13 | $Mo_{12}Fe_{7.5}Bi_2Rb_{0.4}P_{0.3}$ | none | 91.0 | 74.7 | 82.0 |
| Example 39 | $Mo_{12}Fe_{7.5}Bi_2Cs_{0.4}P_{0.3}$ | polyacrylic acid | 88.5 | 76.5 | 86.4 |
| Example 40 | $Mo_{12}Co_3Ni_1Fe_2Bi_1K_{0.5}$ | polyacrylic acid | 77.3 | 67.3 | 87.1 |
| Comparative Example 14 | " | none | 74.3 | 61.1 | 82.2 |
| Example 41 | $Mo_{10}W_2Co_4Fe_1Bi_1K_{0.3}$ | polyacrylic acid | 59.5 | 48.0 | 80.7 |
| Comparative Example 15 | " | none | 29.3 | 24.5 | 83.6 |
| Example 42 | $Mo_{12}Fe_{7.5}Bi_2B_1K_{0.4}$ | polyacrylic acid | 84.7 | 74.8 | 88.3 |
| Comparative Example 16 | " | none | 85.7 | 67.2 | 78.4 |

EXAMPLE 43

18.68 g of ammonium molybdate and 2 g of polyhydroxycarboxylic acid were dissolved under heating in 200 ml of silica sol. Separately, 26.72 g of ferric nitrate, 8.56 g of bismuth nitrate and 1.07 g potassium nitrate were dissolved under heating in 50 ml of nitric acid-acidified silica sol and the thus-formed solution was mixed with the above solution of ammonium molybdate.

In the same manner as described in Example 1, the resulting mixture was molded and calcined to obtain a metal oxide catalyst in which the atomic ratio of the constituent metal elements was expressed as $Mo_{12}Bi_2Fe_{7.5}K_{1.2}$. The same reaction tube as used in Example 1 was charged with 30 ml of the thus-prepared catalyst, and a gaseous mixture containing 3 mole percent of isobutylene, 35.7 mole percent of air and 61.3 mole percent of nitrogen was passed through the reaction tube at a reaction temperature of 370°C. so that the contact time was 1.2 seconds, thereby to effect gas phase catalytic oxidation of isobutylene. The results obtained are shown in Table 9.

EXAMPLE 44

A catalyst was prepared in the same manner as in Example 43 except that polyacrylic acid was used as the macromolecular chelating agent instead of the polyhydroxycarboxylic acid, and gas phase catalytic oxidation of isobutylene was carried out under the same conditions as in Example 43 using the thus-prepared catalyst. The results shown in Table 9 were obtained.

COMPARATIVE EXAMPLE 17

A catalyst was prepared in the same manner as in Example 43 except that no chelating agent was used, and under the same conditions as in Example 43 gas phase catalytic oxidation of isobutylene was carried out by using a gaseous mixture having the same composition as in Example 43 and the thus-prepared catalyst. The results shown in Table 9 were obtained.

lets having a diameter of 5 mm and a length of 3 mm and calcined at 600°C. for 4 hours in an air current. In the thus-obtained metal oxide catalyst, the atomic ratio of the constituent metal elements was expressed as $Mo_{12}Bi_2Fe_{7.5}K_{0.4}$. The ethylenediamine-tetracetic acid added during the catalyst preparation stage disappeared completely during the calcination step. A stainless steel U-shaped reaction tube having an inner diameter of 27 mm was charged with 30 ml of the thus-prepared catalyst and immersed in a salt bath as described in Example 1. A gaseous mixture containing 3 mole percent of isobutylene, 35.7 mole percent of air and 61.3 mole percent of nitrogen was passed through the reaction tube at a reaction temperature of 370°C. so that the contact time was 1.2 seconds. The following results were obtained.

Conversion of isobutylene: 93.99 mole %
Yield of methacrolein: 54.81 mole %
Selectivity to methacrolein: 58.32 mole %

COMPARATIVE EXAMPLE 18

18.68 g of ammonium molybdate was dissolved under heating in 200 ml of silica sol. Separately, 26.72 of ferric nitrate, 8.56 g of bismuth nitrate and 0.35 g of potassium nitrate were dissolved under heating in 50 ml of nitric acid-acidifed silica sol, and the thus-prepared solution was mixed with the above solution of ammonium molybdate. In the same manner as described in Example 45, the liquid mixture was molded into cylindrical pellets and calcined to obtain a metal oxide catalyst in which the atomic ratio of the constituent elements is expressed as $Mo_{12}Bi_2Fe_{7.5}K_{0.4}$. Under the same conditions as described in Example 45, catalytic oxidation of isobutylene was carried out by using a gas mixture having the same composition as in Example 45 and 30 ml of the thus-obtained catalyst. The following results were obtained:

Conversion of isobutylene: 87.25 mole %
Yield of methacrolein: 48.87 mole %
Selectivity to methacrolein: 56.00 mole %

When the results of Example 45 are compared with those of Comparative Example 18, it will readily be Table 9

|  |  | Conversion (mole %) of Isobutylene | Yield (mole %) methacrolein | Selectivity (mole %) to methacrolein |
|---|---|---|---|---|
| Example 43 | polyhydroxycarboxylic acid | 90.67 | 50.64 | 55.85 |
| Example 44 | polyacrylic acid | 96.54 | 49.46 | 51.23 |
| Comparative Example 17 | not added | 65.91 | 35.48 | 53.84 |

EXAMPLE 45

18.68 g of ammonium molybdate [$(NH_4)_6Mo_7O_{24}\cdot 4H_2O$] and 2.58 g of ethylenediamine-tetraacetic acid [$CH_2N(CH_2COOH)_2]_2$ were dissolved under heating in 200 m of silica sol (silica content = 20 wt.%).

Separately, 26.72 g of ferric nitrate [$Fe(NO_3)_3\cdot 9H_2O$], 8.56 g of bismuth nitrate [$(Bi(NO_3)_3\cdot 5H_2O$] and 0.35 g of potassium nitrate ($KNO_3$) were dissolved under heating in 50 ml of nitric acid-acidified silica sol, and the resulting solution was mixed with the above solution of ammonium molybdate. Then, the liquid mixture was heated and concentrated under agitation to form a slurry. The resulting slurry was dried at 120°C. in air, heated at 350°C. to decompose the nitrates, cooled, pulverized, molded into cylindrical pelunderstood that the catalyst of the Mo-Bi-Fe-K system is activated by ethylenediamine-tetraacetic acid and the activity for forming methacrolein is highly improved by addition of the chelating agent in comparison with the comparative catalyst prepared without using the chelating agent.

EXAMPLE 46

A catalyst was prepared in the same manner as in Example 45 except that the amount of potassium nitrate was changed to 1.07 g, and under the same conditions as in Example 45, catalytic oxidation of isobutylene was carried out by using a gaseous mixture having the same composition as in Example 45 and the thus-prepared catalyst. The following results were obtained:

Conversion of isobutylene: 86.65 mole %

Yield of methacrolein: 49.60 mole %
Selectivity to methacrolein: 57.18 mole %

COMPARATIVE EXAMPLE 19

A catalyst was prepared in the same manner as in Comparative Example 18 except that the amount of potassium nitrate was changed to 1.07 g, and under the same conditions as in Example 45, catalytic oxidation of isobutylene was carried out by using a gaseous mixture having the same composition as in Example 45 and the thus-prepared catalyst. The following results were obtained:
Conversion of isobutylene: 65.91 mole %
Yield of methacrolein: 35.48 mole %
Selectivity to methacrolein: 53.84 mole %

EXAMPLE 47

18.68 g of ammonium molybdate and 3.36 g of nitrilotriacetic acid were dissolved under heating in 200 ml of water. Separately, 26.72 g of ferric nitrate, 8.56 g of bismuth nitrate and 0.35 g of potassium nitrate were dissolved under heating in 23 ml of a nitric acid-acidified aqueous solution, and the thus-prepared solution was mixed with the above solution of ammoniun molybdate. Then, 50 g of silica gel pulverized to 150 mesh or smaller was added to the liquid mixture, and the mixture was heated and concentrated under agitation to form a slurry. Subsequent treatments were conducted in the same manner as in Example 45 to obtain a catalyst. Under the same conditions as in Example 45, gas phase catalytic oxidation of isobutylene was carried out by using a gaseous mixture having the same composition as in Example 45 and 30 ml of the thus-prepared catalyst. The results shown in Table 10 were obtained.

EXAMPLE 48

A catalyst was prepared in the same manner as in Example 47 except that 1.54 g of triethylenediamine was used instead of nitrilotriacetic acid, and gas phase catalytic oxidation of isobutylene was carried out in the same manner as in Example 45 by using the thus-prepared catalyst and a gaseous mixture having the same composition as in Example 45. The results shown in Table 10 were obtained.

COMPARATIVE EXAMPLE 19

A catalyst was prepared in the same manner as in Example 47 except that no chelating agent was used, and under the same conditions as in Example 45, gas phase catalytic oxidation of isobutylene was carried out by using the thus-prepared catalyst and a gaseous mixture having the same conditions as in Example 45. The results shown in Table 10 were obtained.

heating in 200 ml of water. Separately, 52.47 g of ferric nitrate, 6.31 g of bismuth nitrate and 0.79 g of potassium nitrate were dissolved under heating in 53 ml of a nitric acid-acidified aqueous solution and this solution was mixed with the above solution of ammonium molybdate. Then, 50 g of silica gel having a particle size of 150 mesh (Japanese Industrial Standard) or smaller was added to the mixture, and the mixture was heated with agitation and concentrated to form a slurry. A catalyst was hereafter prepared by the same procedure as in Example 45.

In the resulting metal oxide catalyst, the atomic ratio of the constituent metals was expressed as $Mo_{12}Fe_{20}Bi_2K_{1.2}$.

Employing 30 ml of the catalyst above obtained, the gas phase catalytic oxidation of isobuthylene was carried out under the same gas reaction composition and the same reaction condition as in Example 45. The following results were obtained:
Conversion of isobutylene: 96.30%
Yield of methacrolein: 71.30%
Selectivity of methacrolein: 74.97%

COMPARATIVE EXAMPLE 20

A catalyst was prepared in the same manner as described in Example 49 except that the ethylenediamine-tetraacetic acid was not used. In the same manner as in Example 45, gas phase catalytic oxidation of isobutylene was conducted by using the thus-obtained catalyst. The following results were obtained:
Conversion of isobutylene: 86.06 mole %
Yield of methacrolein: 64.52 %
Selectivity to methacrolein: 74.97 mole %

The embodiments of the invention in which an exclusive property or privilege is claimed are defined as follows:

1. In a catalyst composition consisting essentially of oxides of elements as active catalyst constituents, wherein said elements comprise molybdenum, bismuth, at least one transition metal selected from the group consisting of iron, nickel and cobalt, an alkali metal selected from the group consisting of potassium, rubidium and cesium, and, optionally, an element selected from the group consisting of boron, phosphorus, arsenic and tungsten, said catalyst composition being prepared by mixing aqueous solutions of water-soluble salts of said elements, and then drying the mixture to obtain the solids and calcining the solids to obtain the catalyst composition, the improvement which comprises: said catalyst composition is prepared by incorporating into at least one of said aqueous solutions a chelating substance selected from the group consisting of organic chelating agents and chelate compounds Table 10

| | Chelating Agent | Conversion (moles %) of isobutylene | Yield (mole %) of methacrolein | Selectivity (mole %) to methacrolein |
|---|---|---|---|---|
| Example 47 | nitrilotriacetic acid | 97.06 | 50.62 | 52.15 |
| Example 48 | triethylenediamine | 95.87 | 49.48 | 51.61 |
| Comparative Example 19 | not added | 84.61 | 45.03 | 53.22 |

EXAMPLE 49

13.77 g of ammonium molybdate and 1.90g of ethylenediamine-tetraacetic acid were dissolved under obtained by reaction between an organic chelating agent and at least one of said elements, said chelating agent being volatilized or combusted during said calcination step.

2. A catalyst composition as claimed in claim 1, in which said catalyst composition is deposited on particles of an inert catalyst carrier.

3. In a process for preparing a catalyst composition consisting essentially of metal oxides as active catalyst constituents, wherein said metals comprise molybdenum, bismuth and at least one transition metal selected from the group consisting of iron, nickel and cobalt, which comprises mixing aqueous solutions of water-soluble salts of said metals, and then drying the mixture to obtain the solids and calcining the solids to obtain the metal oxide catalyst composition, the improvement which comprises: incorporating in at least one of said aqueous solutions a chelating substance selected from the group consisting of organic chelating agents and chelate compounds obtained by reaction between an organic chelating agent and at least one of said metals, said chelating agent being volatilized or combusted during said calcination step.

4. A process as claimed in claim 3, in which an aqueous solution of ammonium molybdate is mixed with an aqueous solution of ferric nitrate and bismuth nitrate.

5. A process as claimed in claim 3, in which an inert catalyst carrier is incorporated into the mixture of said aqueous solutions.

6. In a process for the preparation of acrolein or methacrolein by catalytically oxidizing propylene or isobutylene, respectively, in the gas phase, with a molecular oxygen-containing gas, at a temperature of 250° to 400°C, the improvement which comprises:
conducting the reaction in the presence of a catalyst composition as claimed in claim 1.

* * * * *